United States Patent
Fukuhara et al.

(10) Patent No.: US 8,674,036 B2
(45) Date of Patent: Mar. 18, 2014

(54) HAIR COSMETIC

(75) Inventors: Kazuhisa Fukuhara, Matsudo (JP); Tomoyuki Suzawa, Kawasaki (JP); Kayoko Kitada, Edogawa-ku (JP); Tetsuya Kawai, Higashimurayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/989,201

(22) PCT Filed: Nov. 29, 2011

(86) PCT No.: PCT/JP2011/077558
§ 371 (c)(1),
(2), (4) Date: May 23, 2013

(87) PCT Pub. No.: WO2012/073967
PCT Pub. Date: Jun. 7, 2012

(65) Prior Publication Data
US 2013/0247931 A1    Sep. 26, 2013

(30) Foreign Application Priority Data

Nov. 30, 2010 (JP) ................................. 2010-267473

(51) Int. Cl.
*C08G 77/388* (2006.01)

(52) U.S. Cl.
USPC ........................................................ 525/474

(58) Field of Classification Search
USPC ........................................................ 525/474
See application file for complete search history.

(56) References Cited

U.S. PATENT DOCUMENTS

| | | | |
|---|---|---|---|
| 5,472,689 A * | 12/1995 | Ito | 424/70.122 |
| 5,747,016 A | 5/1998 | Yui et al. | |
| 2006/0045862 A1 | 3/2006 | Tada et al. | |
| 2010/0203002 A1 | 8/2010 | Fukuhara et al. | |
| 2012/0216823 A1 | 8/2012 | Fukuhara et al. | |
| 2012/0220723 A1 | 8/2012 | Fukuhara et al. | |

FOREIGN PATENT DOCUMENTS

| | | |
|---|---|---|
| JP | 7 133352 | 5/1995 |
| JP | 2006 069899 | 3/2006 |
| JP | 2009 24114 | 2/2009 |
| JP | 2009 256367 | 11/2009 |
| WO | 2011 062077 | 5/2011 |
| WO | 2011 062210 | 5/2011 |

OTHER PUBLICATIONS

International Search Report Issued Feb. 21, 2012 in PCT/JP11/077558 Filed Nov. 29, 2011.

* cited by examiner

*Primary Examiner* — Mike M Dollinger
(74) *Attorney, Agent, or Firm* — Oblon, Spivak, McClelland, Maier & Neustadt, L.L.P.

(57) ABSTRACT

A hair cosmetic composition comprising components (A) and (B) at a mass ratio of (A)/(B)=0.66 to 9.0: (A) an organopolysiloxane wherein poly(acylalkyleneimine) segments each having a molecular weight of from 1,200 to 5,500 are bound to an organopolysiloxane segment having a molecular weight of from 7,000 to 100,000, the mass ratio of the both segments is from 35/65 to 60/40, and the organopolysiloxane segment between the above-mentioned bonds has a molecular weight of from 1,300 to 5,500, (B) an organopolysiloxane wherein poly(acylalkyleneimine) segments each having a molecular weight of from 800 to 1,600 are bound to an organopolysiloxane segment having a molecular weight of from 10,000 to 100,000, the mass ratio of the both segments is from 65/35 to 82/18, and the organopolysiloxane segment between the above-mentioned bonds has a molecular weight of from 1,500 to 3,500.

12 Claims, No Drawings

HAIR COSMETIC

CROSS REFERENCE TO RELATED APPLICATION

This application is a 371 of PCT/JP2011/077558, filed on Nov. 29, 2011, and claims priority to Japanese Patent Application No. 2010-267473, filed on Nov. 30, 2010.

FIELD OF THE INVENTION

The present invention relates to a hair cosmetic composition comprising organopolysiloxanes having specific structures at a specific ratio.

BACKGROUND OF THE INVENTION

Various forms of organopolysiloxanes are used as agents for improving feel for touch in, for example, shampoos and hair conditioners, because of having a number of excellent characteristics. For example, Patent Document 1 discloses a hair setting agent composition comprising a poly(N-acylalkyleneimine)-modified organopolysiloxane, which does not cause breaking or plastic modification within a predetermined range of elongation rate. This hair setting agent shows excellent performances such as: the hair setting agent is excellent in hair setting ability and retention thereof, the hair setting agent can provide fine feel for touch with soft feeling and without coarse feeling to the hair after hair setting, and the hair setting agent can be easily washed away by hair wash, as compared to conventional hair setting agent compositions using film-forming resins. However, this hair setting agent composition cannot provide sufficient ability of retaining a hair style in the case when the hair is combed with fingers after setting.

Furthermore, Patent Document 2 discloses a poly(N-acylalkyleneimine)-modified organopolysiloxane having different characteristics, for example, different modification ratio, from those used in Document 1, and shows excellent expansibility and also excellent solubility and dispersibility in water or lower alcohols. A hair cosmetic composition comprising this organopolysiloxane can provide fine feeling, flexibility enough to protect the hair style from disturbing by external factors (e.g. combing of the hair with fingers, wind, vibration), and a natural finish. However, the physical properties of this organopolysiloxane around room temperature are soft, thus the organopolysiloxane is not suitable for the purposes of providing a fluffy volume to a hair style and retaining the volume, and preventing flyaways, unwanted curls or kinks (also referred to as "frizzy hair" in English) to provide and retain manageability to the hair.

CITATION LIST

Patent Documents

Patent Document 1: JP-A-07-133352
Patent Document 2: JP-A-2009-24114

SUMMARY OF THE INVENTION

The present invention provides a hair cosmetic composition comprising the following components (A) and (B) at a mass ratio of (A)/(B)=0.66 to 9.0:

component (A): an organopolysiloxane, wherein poly(N-acylalkyleneimine) segments consisting of repeating units represented by the following general formula (1);

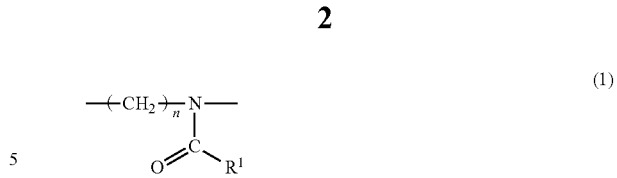

wherein $R^1$ represents a hydrogen atom, an alkyl group having 1 to 22 carbon atoms, an aralkyl group or an aryl group, and n represents 2 or 3, are bound to at least two silicon atoms of an organopolysiloxane segment that constitutes a main chain via alkylene groups containing heteroatoms, wherein the number average molecular weight of the poly(N-acylalkyleneimine) segments is from 1,200 to 5,500, the mass ratio of (a) the organopolysiloxane segment that constitutes the main chain and (b) the poly(N-acylalkyleneimine) segments (a/b) is from 35/65 to 60/40, the weight average molecular weight of the organopolysiloxane segment between the adjacent poly(N-acylalkyleneimine) segments is from 1,300 to 5,500, and the weight average molecular weight of the organopolysiloxane segment that constitutes the main chain is from 7,000 to 100,000; and component (B): an organopolysiloxane, wherein poly(N-acylalkyleneimine) segments consisting of repeating units represented by the above-mentioned general formula (1) are bound to at least two silicon atoms of an organopolysiloxane segment that constitutes a main chain via alkylene groups containing heteroatoms, wherein the number average molecular weight of the poly(N-acylalkyleneimine) segments is from 800 to 1,600, the mass ratio of (a) the organopolysiloxane segment that constitutes the main chain and (b) the poly(N-acylalkyleneimine) segments (a/b) is from 65/35 to 82/18, the weight average molecular weight of the organopolysiloxane segment between the adjacent poly(N-acylalkyleneimine) segments is from 1,500 to 3,500, and the weight average molecular weight of the organopolysiloxane segment that constitutes the main chain is from 10,000 to 100,000.

Furthermore, the present invention provides a method for treating hair, comprising applying the above-mentioned hair cosmetic composition onto the hair, and blow-drying or natural drying without rinsing the hair cosmetic composition away.

DETAILED DESCRIPTION OF THE INVENTION

The present invention relates to a hair cosmetic composition that can provide soft feeling and natural finish feeling to the hair, can be preferably used for the purposes of providing a fluffy volume to a hair style, and preventing flyaways, unwanted curls or kinks hair to provide manageability to the hair, and can maintain a hair style for a long time without disturbing the hair style by external factors (e.g. combing of the hair with fingers, wind, vibration).

The present inventors found that a hair cosmetic composition that satisfies all of the above-mentioned performances can be obtained by incorporating two kinds of poly(N-acylalkyleneimine)-modified organopolysiloxanes having specific structures at a specific ratio.

[Component (A): The First Organopolysiloxane]

The organopolysiloxane of component (A) has a specific structure in which poly(N-acylalkyleneimine) segments are bound to at least two silicon atoms of the organopolysiloxane segment that constitutes a main chain at a predetermined interval and a predetermined ratio via alkylene groups containing heteroatoms. Specifically, the poly(N-acylalkyleneimine) segments having high hydrophilicity and the organopolysiloxane segment having high oleophilicity are present at a specific ratio, and the poly(N-acylalkyleneimine) segments are present at specific intervals.

At least two poly(N-acylalkyleneimine) segments can be bound via alkylene groups containing heteroatoms to any of the silicon atoms that constitute the organopolysiloxane segment, preferably the poly(N-acylalkyleneimine) segments are bound to one or more silicon atoms other than silicon atoms at both terminals via the above-mentioned alkylene groups, more preferably the poly(N-acylalkyleneimine) segments are bound to two or more silicon atoms other than silicon atoms at both terminals via the above-mentioned alkylene groups.

The alkylene group containing heteroatoms functions as a linking group for the poly(N-acylalkyleneimine) segments. Examples of such alkylene groups include alkylene groups having 2 to 20 carbon atoms and containing 1 to 3 nitrogen atoms, oxygen atoms or sulfur atoms, a group represented by any of the following general formulas (i) to (viii) is preferable, and a group represented by any of the following general formulas (i) to (iii) is more preferable. In the formulas, $An^-$ represents a counterion of a quaternary ammonium salt, and examples may include ethyl sulfate ion, methyl sulfate ion, chloride ion, iodide ion, sulfate ion, p-toluenesulfonate ion and perchlorate ion.

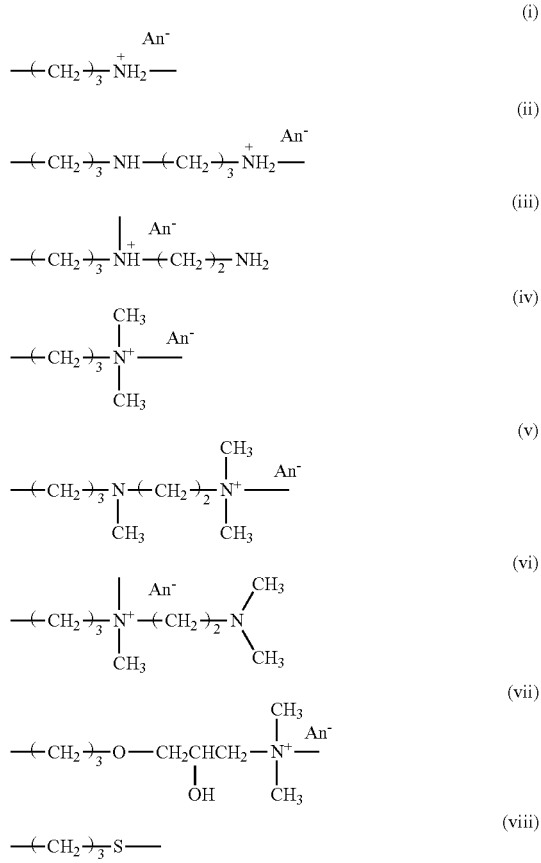

In the N-acylalkyleneimine unit that constitutes the poly(N-acylalkyleneimine) segment, examples of the alkyl group having 1 to 22 carbon atoms in $R^1$ in the general formula (1) include linear, branched or cyclic alkyl groups having 1 to 22 carbon atoms, and specifically include, for example, a methyl group, an ethyl group, a n-propyl group, an isopropyl group, a n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group, and docosyl group. Among these, alkyl groups having 1 to 10 carbon atoms are preferable, alkyl groups having 1 to 6 carbon atoms are more preferable, and alkyl groups having 1 to 3 carbon atoms are even more preferable from the viewpoint of high solubility in water or lower alcohols.

Examples of the aralkyl group include aralkyl groups having 7 to 15 carbon atoms, and specifically include, for example, a benzyl group, a phenethyl group, a trityl group, a naphthylmethyl group, and an anthracenylmethyl group. Among these, aralkyl groups having 7 to 14 carbon atoms are preferable, and aralkyl groups having 7 to 10 carbon atoms are more preferable.

Examples of the aryl group include aryl groups having 6 to 14 carbon atoms, and specifically include, for example, a phenyl group, a tolyl group, a xylyl group, a naphthyl group, a biphenyl group, an anthryl group, and a phenanthryl group. Among these, aryl groups having 6 to 12 carbon atoms are preferable, and aryl groups having 6 to 9 carbon atoms are more preferable.

Among these, $R^1$ is preferably alkyl groups having 1 to 6 carbon atoms, and more preferably alkyl groups having 1 to 3 carbon atoms.

The mass ratio of (a) the organopolysiloxane segment and (b) the poly(N-acylalkyleneimine) segments (a/b) in component (A) is from 35/65 to 60/40, and is preferably from 42/58 to 58/42, more preferably from 45/55 to 55/45, even more preferably from 47/53 to 53/47, from the viewpoint of making the hair cosmetic composition more suitable for expressing the effects of the present invention: providing solubility and dispersibility in the solvent to the hair cosmetic composition, providing preferable feeling to the hair after hair styling, and providing suitable elasticity suitable for setting and retaining hair style, in good balance.

In the present specification, the mass ratio (a/b) refers to a value obtained by dissolving 5 mass % of the organopolysiloxane of the present invention in deuterated chloroform, and obtaining the integral ratio of the alkyl groups or phenyl groups in the organopolysiloxane segment and the methylene groups in the poly(N-acylalkyleneimine) segments using nuclear magnetic resonance ($^1$H-NMR) analysis.

Furthermore, the organopolysiloxane segment between the adjacent poly(N-acylalkyleneimine) segments has a weight average molecular weight (MWg) of from 1,300 to 5,500, preferably from 1,600 to 3,500, more preferably from 1,800 to 3,200, even more preferably from 2,000 to 3,000.

In the present specification, "the organopolysiloxane segment between the adjacent poly(N-acylalkyleneimine) segments" refers to a part between the two points from the binding point of the poly(N-acylalkyleneimine) segment to the organopolysiloxane segment (binding point α) to the binding point of the adjacent poly(N-acylalkyleneimine) segment (binding point β), which is constituted by one $R^2SiO$ unit, one $R^6$ and (y+1) $(R^2)_2SiO$ units, as shown in the following formula (2) (a part surrounded by a broken line). Furthermore, "the poly(N-acylalkyleneimine) segment" refers to —W—$R^7$ that is bound to the above-mentioned $R^6$.

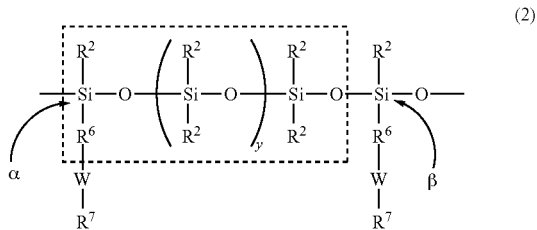

(2)

In the above-mentioned general formula (2), $R^2$s each independently represent an alkyl group having 1 to 22 carbon atoms or a phenyl group, $R^6$ represents an alkylene group containing heteroatoms, —W—$R^7$ represents a poly(N-acylalkyleneimine) segment, $R^7$ represents a residue of a polymerization initiator, and y represents a positive number.

MWg is the molecular weight of the part surrounded by the broken line in the above-mentioned general formula (2), and can be interpreted as the mass (g/mol) of the organopolysiloxane segment per 1 mole of the poly(N-acylalkyleneimine) segments. In addition, when 100% of the functional groups in the modified organopolysiloxane, which is a raw material compound, are substituted by poly(N-acylalkyleneimine), the mass is identical with the functional group equivalent amount (g/mol) of the modified organopolysiloxane.

Although the molecular weight (MWox) of the poly(N-acylalkyleneimine) segment can be measured by calculating from the molecular weight and polymerization degree of the N-acylalkyleneimine unit, or by a measurement using gel permeation chromatography (GPC) mentioned below, the molecular weight shall mean a number average molecular weight measured by a GPC measurement method in the present invention. The MWox of component (A) is from 1,200 to 5,500, preferably from 1,600 to 3,500, more preferably from 1,800 to 3,200, even more preferably from 2,000 to 3,000. Accordingly, it is possible to impart hardness and fine feeling that are preferable for imparting a fluffy volume to the hair and for preventing flyaways, unwanted curls or kinks to provide manageability to the hair, and are sufficient for maintaining these hair styles at normal temperature (around ordinary temperature) at which people live.

Furthermore, MWg can be obtained by the following formula (I) by using content ratio of the organopolysiloxane segment that constitutes the main chain (Csi).

$$MWg = \frac{Csi \times MWox}{100 - Csi} \quad (I)$$

The organopolysiloxane segment that constitutes the main chain has a weight average molecular weight (MWsi) of from 7,000 to 100,000, and has a weight average molecular weight of preferably from 10,000 to 80,000, more preferably from 20,000 to 60,000, even more preferably from 30,000 to 50,000, from the viewpoints of solubility in polar solvents such as water and easy handling after dissolution. The MWsi is approximately the same as the weight average molecular weight of the modified organopolysiloxane as a raw material compound, since the MWsi has a common backbone with the modified organopolysiloxane, the raw material compound. The average molecular weight of the modified organopolysiloxane as a raw material compound is obtained by measuring by GPC under the following measurement conditions and polystyrene conversion.

Column: Super HZ4000+Super HZ2000 (manufactured by Tosoh Corporation)
Eluent: 1 mM triethylamine/THF
Flow amount: 0.35 mL/min
Column temperature: 40° C.
Detector: UV
Sample: 50 μL The organopolysiloxane of component (A) has a weight average molecular weight (MWt) of preferably from 10,000 to 200,000, more preferably from 30,000 to 100,000, even more preferably from 50,000 to 70,000. Accordingly, fine feeling can be imparted to the hair, and the solubility in a polar solvent such as water becomes excellent. Furthermore, the setting property and set retention can further be improved. In the present invention, MWt can be obtained from the weight average molecular weight of the modified organopolysiloxane as a raw material compound, and the above-mentioned mass ratio (a/b).

Subsequently, the method for the production of the organopolysiloxane of component (A) is explained below.

The organopolysiloxane of component (A) is produced, for example, by reacting a modified organosiloxane represented by the following general formula (3):

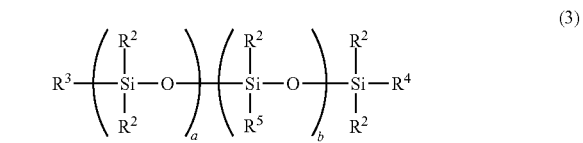

(3)

wherein $R^2$ is defined as above, $R^3$ and $R^4$ each independently represent a group that is identical with $R^2$, or a monovalent group represented by any of the following general formulas (ix) to (xiv):

(ix)

(x)

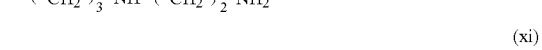

(xi)

(xii)

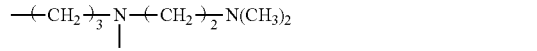

(xiii)

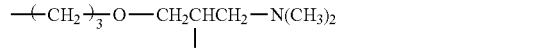

(xiv)

$R^5$ represents a monovalent group represented by the above-mentioned formula (ix) to (xiv), a represents an integer of from 89 to 1332, and b represents an integer of from 2 to 77, with an end-reactive poly(N-acylalkyleneimine) that is obtained by ring-opening polymerization of a cyclic imino ether represented by the following general formula (4):

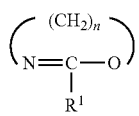

(4)

wherein R¹ and n are defined as above (hereinafter referred to as "cyclic imino ether (4)").

It is desirable to use the modified organopolysiloxane (3) having a functional group equivalent amount of preferably from 1,700 to 3,500, more preferably from 1,800 to 3,200, even more preferably from 2,000 to 3,000, and a weight average molecular weight of preferably from 7,000 to 100,000, more preferably from 10,000 to 80,000, even more preferably from 30,000 to 50,000. The above-mentioned weight average molecular weight of the modified organopolysiloxane (3) as a raw material is approximately identical with the weight average molecular weight (MWsi) of the above-mentioned organopolysiloxane segment that constitutes the above-mentioned main chain.

Furthermore, it is desirable to adjust the molecular weight of the end-reactive poly(N-acylalkyleneimine) to preferably from 1,200 to 5,500, preferably from 1,600 to 3,500, more preferably from 1,800 to 3,200, even more preferably from 2,000 to 3,000. This is approximately the same as the molecular weight (MWox) of the above-mentioned poly(N-acylalkyleneimine) segment.

A polymerization initiator can be used for the open-ring polymerization of the cyclic imino ether (4). As the polymerization initiator, compounds having strong electrophilic reactivity such as alkyl esters of strong acids such as benzenesulfonic acid alkyl esters, p-toluenesulfonic acid alkylesters, trifluoromethanesulfonic acid alkyl esters, trifluoroacetic acid alkyl esters, and sulfonic acid dialkyl esters can be used, and among these, dialkyl sulfates are preferably used. The amount of use of the polymerization initiator is generally 1 mol of the polymerization initiator with respect to 2 to 100 moles of the cyclic imino ether (4).

As the polymerization solvent, for example, acetate esters such as ethyl acetate and propyl acetate, ethers such as diethyl ether, diisopropyl ether, dioxane and tetrahydrofuran, ketones such as acetone and methyl ethyl ketone, halogen solvents such as chloroform and methylene chloride, nitrile-based solvents such as acetonitrile and benzonitrile, and aprotic polar solvents such as N,N-dimethylformamide, N,N-dimethylacetamide and dimethylsulfoxide can be used, and among these, acetate esters are preferably used. The amount of use of the solvent is generally from 20 to 2,000 parts by mass with respect to 100 parts by mass of the cyclic imino ether (4).

The temperature for polymerization is generally from 30 to 170° C., and preferably 40 to 150° C., and the time for polymerization may be varied depending on, for example, the polymerization temperature, generally is from 1 to 60 hours.

For example, when a 2-substituted-2-oxazoline is used as the cyclic imino ether (4), then a poly(N-acylethyleneimine) wherein n=2 in the above-mentioned general formula (1) can be obtained, while, when a 2-substituted-dihydro-2-oxazine is used, a poly(N-acylpropyleneimine) wherein n=3 in the above-mentioned general formula (1) can be obtained.

As the method for connecting the poly(N-acylalkyleneimine) and organopolysiloxane segment, for example, the following methods are exemplified.

1) A method comprising reacting an end-reactive poly(N-acylalkyleneimine) that is obtained by living polymerization of a cyclic imino ether with the modified organopolysiloxane represented by the general formula (3)

2) A reaction for forming an ester by condensation of a carboxyl group and a hydroxyl group 3) A reaction for forming an amide by condensation of a carboxyl group and an amino group 4) A reaction between a halogenated alkyl group and a primary, secondary or tertiary amino group for forming a secondary, tertiary or quaternary ammonium 5) An addition reaction of a vinyl group to an organopolysiloxane having an Si—H group 6) A reaction for forming a β-hydroxylamine between an epoxy group and an amino group Of these, the method of the above-mentioned 1) is remarkably effective in that the polymerization degree can be easily controlled by the amounts of use of the cyclic imino ether (4) and polymerization initiator as in the theoretical formula (II) shown below, and a poly(N-acylalkyleneimine), showing approximately monodispersion with narrower molecular weight distribution than those obtained in general radical polymerization, can be obtained.

$MWi$=Molar number of cyclic imino ether/Molar number of polymerization initiator×Molecular weight of cyclic imino ether+Molecular weight of polymerization initiator   (II)

[MWi: Molecular Weight of Poly(N-Acylalkyleneimine)]

The organopolysiloxane of component (A) has a specific structure in which poly(N-acylalkyleneimine) segments are bound to at least two silicon atoms of an organopolysiloxane segment having a predetermined molecular weight via alkylene groups containing heteroatoms at predetermined intervals and a predetermined ratio. Accordingly, natural finish with suitable elasticity suitable for setting and retaining a hair style around an ordinary temperature, fine feeling, and fastness against applied external force, can be obtained. Furthermore, the organopolysiloxane can be dissolved in polar solvents such as water and lower alcohols.

Preferable examples of the organopolysiloxane of component (A) may include, for example, poly(N-formylethyleneimine)organosiloxane, poly(N-acetylethyleneimine)organosiloxane, and poly(N-propionylethyleneimine)organosiloxane.

The organopolysiloxanes of component (A) may be used alone or in combination of two or more, and the content thereof is preferably from 0.01 to 30 mass %, more preferably from 0.05 to 20 mass %, even more preferably from 0.1 to 10 mass %, even more preferably from 0.5 to 5 mass % on the basis of the total mass of the hair cosmetic composition, from the viewpoints of hair setting property, set retention property and washing property. Furthermore, by adjusting the content to such a degree, two styling properties, setting property and set retention property, in the case of combination with component (B) mentioned below, can further be improved.

[Component (B): The Second Organopolysiloxane]

In the organopolysiloxane of component (B), the poly(N-acylalkyleneimine) segments consisting of the repeating unit represented by the above-mentioned general formula (1) are bound to at least two silicon atoms of the organopolysiloxane segment that constitutes the main chain via alkylene groups containing heteroatoms, in a similar manner to that in component (A). Therefore, component (A) and component (B) have similar structures to each other, and are both referred to as "poly silicone-9" in INCI (International Nomenclature of Cosmetic Ingredients), whereas the organopolysiloxane of component (B) differs from the organopolysiloxane of component (A) in the following aspects.

i) The mass ratio of (a) the organopolysiloxane segment and (b) the poly(N-acylalkyleneimine) segments (a/b) is from 65/35 to 82/18.

The a/b is preferably from 68/32 to 80/20, even more preferably from 70/30 to 79/21, even more preferably from 73/27 to 79/21, from the viewpoint of formation of a suitable continuous film on the surface of the hair to ensure weak surface adhesiveness on the hair.

ii) The weight average molecular weight (MWg) of the organopolysiloxane segment between the adjacent poly(N-acylalkyleneimine) segments is from 1,500 to 3,500.

MWg is preferably from 1,600 to 3,200, more preferably from 1,700 to 3,000, from the viewpoint of formation of a suitable continuous film on the surface of the hair to ensure weak surface adhesiveness on the hair.

iii) The poly(N-acylalkyleneimine) segments each have a number average molecular weight (MWox) of from 800 to 1,600.

MWox is preferably from 850 to 1,500, more preferably from 900 to 1,400, from the viewpoint of formation of a suitable continuous film on the surface of the hair to ensure weak surface adhesiveness on the hair.

iv) The organopolysiloxane segment that constitutes the main chain has a weight average molecular weight (MWsi) of from 10,000 to 100,000.

MWsi is preferably from 20,000 to 80,000, more preferably from 30,000 to 60,000, from the viewpoint of formation of a suitable continuous film on the surface of the hair to ensure weak surface adhesiveness on the hair and further ensure solubility in polar solvent such as water and easy handling after dissolution.

Furthermore, the organopolysiloxane of component (B) has a weight average molecular weight (MWt) of preferably from 12,000 to 150,000, more preferably from 24,000 to 120,000, even more preferably from 37,000 to 92,000. Accordingly, a suitable continuous film can be formed on the surface of the hair to ensure weak surface adhesiveness on the hair, and excellent solubility in polar solvents such as water can be obtained.

The organopolysiloxane of component (B) can be produced, for example, by reacting a modified organopolysiloxane wherein a is an integer from 135 to 1350 and b is an integer from 3 to 57 in the above-mentioned general formula (3), with an end-reactive poly(N-acylalkyleneimine) obtained by open-ring polymerization of the cyclic imino ether (4).

It is desirable to use a modified organopolysiloxane having a functional group equivalent amount of preferably from 1,700 to 3,500, more preferably from 1,800 to 3,200, even more preferably from 2,000 to 3,000, and a weight average molecular weight of preferably from 10,000 to 100,000, more preferably from 20,000 to 80,000, even more preferably from 30,000 to 60,000.

Furthermore, it is desirable to adjust the molecular weight of the end-reactive poly(N-acylalkyleneimine) to preferably from 800 to 1,600, more preferably from 850 to 1,500, even more preferably from 900 to 1,400.

Except for these aspects, the organopolysiloxane of component (B) can be produced in a similar manner to that in the production of the organopolysiloxane of the above-mentioned component (A).

The organopolysiloxanes of component (B) may be used alone or in combination of two or more, and the content thereof is preferably from 0.001 to 30 mass %, more preferably from 0.005 to 20 mass %, even more preferably from 0.01 to 10 mass %, even more preferably from 0.05 to 5 mass % on the basis of the total mass of the hair cosmetic composition, from the viewpoint of forming a suitable continuous film on the surface of the hair to ensure weak surface adhesiveness on the hair, obtaining hair setting property and retention of the same, while retaining washing property. Furthermore, by adjusting the content to such degree, two styling properties, setting property and set retention property, in the case of combination with component (A), can further be improved.

As mentioned above, the organopolysiloxanes of component (A) and component (B) have similar structures, however have different properties; the organopolysiloxane of component (A) provides suitable elasticity suitable for setting and retaining a hair style around an ordinary temperature, whereas the organopolysiloxane of component (B) provides weak surface adhesiveness.

The content mass ratio of component (A) and component (B) in the hair cosmetic composition of the present invention, (A)/(B), is adjusted to 0.66 to 9.0 from the viewpoint of excellent effects of imparting a volumy hair style, prevention of flyaways and fine retention of a finished hairstyle, and is adjusted to preferably from 0.90 to 7.0, more preferably from 1.0 to 5.6, even more preferably from 1.0 to 4.0. The abovementioned effects of the present invention can be obtained by combining component (A) and component (B) at the abovementioned ratio, and such effects cannot be obtained even if a single organopolysiloxane (poly silicone-9) showing approximately the same value as an average value of combination of the two components is used.

Specifically, the present inventors found that the film formed on the surface of the hair has the following properties by combination of component (A) and component (B). These two kinds of organopolysiloxanes (A) and (B) having different structures are homogeneously dissolved each other in the hair cosmetic composition, whereas they become incompatible each other during formation of the film. Since the organopolysiloxane (B) having a higher silicone ratio segregates on the surface of the organopolysiloxane (A), the formed film has specific physical properties wherein the physical properties of the organopolysiloxane (A) that form the continuous layer are dominant as a bulk characteristic, while the physical properties of the segregated organopolysiloxane (B) are dominant as a surface physical property.

The film formed in the case of mixing the two components in the range of mass ratio (A)/(B) of from 0.66 to 9.0, the weak adhesiveness of the organopolysiloxane (B) on the surface layer and the elasticity of the organopolysiloxane (A) in the continuous layer are well-balanced, and thus imparting a volumy hair style, preventing flyaways, and more excellent retention of a finished hair style are provided. In the range of the ratio of from 1.0 to 5.6, the structure of the continuous layer of component (A) becomes firm. In the case when the mass ratio (A)/(B) is more than 9.0, the amount of the organopolysiloxane (B) that forms the surface layer of the film is too small and thus the adhesiveness on the hair becomes insufficient, and the retention of the hair style becomes poor. On the other hand, when the mass ratio (A)/(B) is from 0 to lower than 0.66, the organopolysiloxane (B) forms a continuous layer, and the bulk characteristic is dominated by the physical properties of the organopolysiloxane (B). Consequently, the elasticity of the film significantly decreases, and thus a volumy hair style and an ability of preventing flyaways are provided insufficiently.

[Lower Alcohol]

The hair cosmetic composition of the present invention may further contain an aliphatic alcohol having 1 to 6 carbon atoms. The content of the aliphatic alcohol having 1 to 6 carbon atoms is preferably from 0.01 to 98 mass %, more preferably from 0.1 to 90 mass %, even more preferably from 0.5 to 75 mass % in the hair cosmetic composition of the present invention. Accordingly, the fitting property of this hair cosmetic composition to the hair is improved, and thus a volumy hair style and prevention of flyaways can be obtained more effectively.

[Cationic Surfactant]

It is preferable to further incorporate a cationic surfactant into the hair cosmetic composition of the present invention. As the cationic surfactant, a quaternary ammonium salt represented by the following general formula (5) may be exemplified.

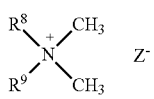
(5)

wherein $R^8$ and $R^9$ each independently represent a hydrogen atom, an alkyl group having 1 to 28 carbons or a benzyl group, with the proviso that the case when $R^8$ and $R^9$ are simultaneously hydrogen atoms or benzyl groups, and the case when $R^8$ and $R^9$ are simultaneously lower alkyl groups having 1 to 3 carbon atoms are excluded, and $Z^-$ represents an anion.

It is preferable that one of $R^8$ and $R^9$ is a linear or branched alkyl group, further a linear alkyl group, which has 14 to 24 carbon atoms, and the other is a lower alkyl group having 1 to 3 carbon atoms, further a methyl group. The anion $Z^-$ may be, for example, halogenated ions such as chloride ion and bromide ion; organic anions such as ethyl sulfate ion and methyl carbonate ion, halogenated ions are preferable, and chloride ions are more preferable.

Preferable examples of the cationic surfactant include, for example, mono-long chain alkyl quaternary ammonium salts, and specific examples may include cetyl trimethylammonium chloride, stearyl trimethylammonium chloride, arachyl trimethylammonium chloride, behenyl trimethylammonium chloride, and among these, stearyl trimethylammonium chloride and behenyl trimethylammonium chloride are more preferable.

These cationic surfactants may be used alone or in combination of two or more, and the content thereof is preferably from 0.01 to 10 mass %, more preferably from 0.05 to 5 mass % in the hair cosmetic composition of the present invention. Accordingly, the film by component (A) and component (B) may adhere to the hair homogeneously, and thus the fitting property of the hair cosmetic composition with the hair may be improved, the smoothness of the hair during hair styling may be improved, and the effect of imparting a volume to a hair style and the effect of preventing flyaways may become more effective.

[Other Surfactants]

Surfactant other than the cationic surfactant may be incorporated in the hair cosmetic composition of the present invention, from the viewpoint of improvement of the stability of the system such as solubilization and dispersion property in solvent. Such surfactants may include a nonionic surfactant, an amphoteric surfactant and an anionic surfactant.

Examples of the nonionic surfactant may include, for example, polyoxyalkylene alkyl ethers, polyoxyalkylene alkenyl ethers, higher aliphatic acid sucrose esters, polyglycerin aliphatic acid esters, mono- or di-ethanolamides of higher aliphatic acids, polyoxyethylene hydrogenated castor oil, polyoxyethylene sorbitan aliphatic acid esters, polyoxyethylene sorbit aliphatic acid esters, alkylsaccharide-based surfactants, alkylamine oxides, and alkylamideamine oxides. Among these, polyoxyalkylene alkyl ethers and polyoxyethylene hydrogenated castor oil are preferable, and polyoxyethylene alkyl ethers are more preferable.

Examples of the amphoteric surfactants may include, for example, imidazoline-based, carbobetaine-based, amidobetaine-based, sulfobetaine-based, hydroxysulfobetaine-based and amidosulfobetaine-based amphoteric surfactants.

Examples of the anionic surfactant may include, for example, alkylbenzenesulfonates, alkyl or alkenyl ether sulfates, alkyl or alkenyl sulfates, olefin sulfonates, alkanesulfonates, saturated or unsaturated aliphatic acid salts, alkyl or alkenyl ether carboxylates, α-sulfoaliphatic acid salts, N-acylaminoacid-type surfactants, phosphate mono- or diester-type surfactants, and sulfosuccinic acid esters. Examples of the counterions of the anionic residues of the above-mentioned surfactant may include alkali metal ions such as sodium ion and potassium ion; alkaline earth metal ions such as calcium ion and magnesium ion; ammonium ion; alkanolamines having 1 to 3 alkanol groups having 2 or 3 carbon atoms (for example, monoethanolamine, diethanolamine, triethanolamine, triisopropanolamine). Furthermore, examples of the counterions of the cationic residue may include halogenated ions such as chloride ion, bromide ion and iodide ion, methosulfate ion and saccharinate ion.

These surfactants other than the cationic surfactant may be used alone or in combination of two or more, and the content thereof is preferably from 0.01 to 10 mass %, more preferably 0.05 to 5 mass % in the hair cosmetic composition of the present invention, from the viewpoint of improvement of the stability of the system, including, for example, solubilization property in a solvent, and emulsification of an oil agent.

[Set Polymer]

Furthermore, when a set polymer is incorporated in the hair cosmetic composition of the present invention, the set retention force is further improved and the slip feeling of the hair becomes fine.

Examples of the set polymer may include those shown in the following 1) to 10), and these may be used alone or by combining two or more kinds.

1) Vinylpyrrolidone-Based Polymer

Polyvinylpyrrolidone

As commercially available products, for example, Luviskol K12 and K30 (these are manufactured by BASF), PVP K15 and K30 (these are manufactured by GAF) may be exemplified.

Vinylpyrrolidone/Vinyl Acetate Copolymer

As commercially available products, for example, Luviskol VA28, VA64 and VA73 (these are manufactured by BASF), PVP/VA E-735 and S-630 (these are manufactured by GAF) may be exemplified.

Vinylpyrrolidone/Vinyl Acetate/Vinyl Propionate Ternary Copolymer

As commercially available products, for example, Luviskol VAP343 (manufactured by BASF) may be exemplified.

Vinylpyrrolidone/Alkylaminoacrylate Copolymer

As commercially available products, for example, Luviflex (manufactured by BASF), Copolymer 845, 937 and 958 (these are manufactured by GAF) may be exemplified.

Vinylpyrrolidone/Acrylate/(Meth)Acrylic Acid Copolymer

As commercially available products, for example, Luviflex VBM35 (manufactured by BASF) may be exemplified.

Vinylpyrrolidone/Alkylamino Acrylate/Vinylcaprolactam Copolymer

As commercially available products, for example, Copolymer VC-713 (manufactured by GAF) may be exemplified.

2) Acidic Vinyl Ether-Based Polymer

Methyl Vinyl Ether/Maleic Anhydride Alkyl Half Ester Copolymer

As commercially available products, for example, Gantrez ES-225, ES-425 and SP-215 (these are manufactured by GAF) may be exemplified.

3) Acidic Polyvinyl Acetate-Based Polymer

Vinyl Acetate/Crotonic Acid Copolymer

As commercially available products, for example, Resin 28-1310 (manufactured by National Starch), Luviset CA66 (manufactured by BASF) may be exemplified.

Vinyl Acetate/Crotonic Acid/Vinyl Neodecanoate Copolymer

As commercially available products, for example, Resin 28-2930 (manufactured by National Starch) may be exemplified.

Vinyl Acetate/Crotonic Acid/Vinyl Propionate Copolymer

As commercially available products, for example, Luviset CAP (manufactured by BASF) may be exemplified.

4) Acidic Acrylic-Based Polymer (Meth)Acrylic Acid/(Meth)Acrylic Acid Ester Copolymer As commercially available products, for example, PLAS-SIZE L53P (manufactured by Goo Chemical Co., Ltd.), DIA-HOLD (manufactured by Mitsubishi Petrochemical Co., Ltd.) may be exemplified.

Acrylic Acid/Acrylic Acid Alkyl Ester/Alkylacrylamide Copolymer

As commercially available products, for example, Ultrahold 8 (manufactured by BASF), Unfoamer V-42 (manufactured by National Starch) may be exemplified.

5) Amphoteric Acrylic-Based Polymer (Meth)Acryl Ethyl Betaine/(Meth)Acrylic Acid Alkyl Ester Copolymer For example, a copolymer of N-methacryloyloxyethyl-N, N-dimethylammonium-α-N-methylcarboxybetain e and a (meth)acrylic acid alkyl ester are exemplified, and as commercially available products, for example, Yukaformer M-75 and SM (these are manufactured by Mitsubishi Petrochemical Co., Ltd.) may be exemplified.

Acrylic Acid Alkyl Ester/Butylaminoethyl Methacrylate/Acrylic Acid Octylamide Copolymer For example, a copolymer of octylacrylamide/acrylate/butylaminoethyl methacrylate copolymer is exemplified, and as commercially available products, for example, Unfoamer 28-4910 (manufactured by National Starch) may be exemplified.

6) Basic Acrylic-Based Polymer

Acrylamide-Acrylic Ester-Based Copolymer

Examples may include those described in the Examples of JP-A No. 2-180911 and JP-A No. 8-291206.

7) Cellulose Derivative

Cationic Cellulose Derivative

As commercially available products, for example, Celquat H-100 and L-200 (manufactured by National Starch) may be exemplified.

8) Chitin/Chitosan Derivative

Hydroxypropylchitosan

As commercially available products, for example, Chitofilmer (manufactured by Ichimaru Pharcos Co., Ltd.) may be exemplified.

9) Salt of Carboxymethylchitin, Carboxymethylchitosan or Chitosan with Monoacid Such as Pyrrolidonecarboxylic Acid, Lactic Acid and Glycolic Acid or Diacid Such as Adipic Acid and Succinic Acid As commercially available products, for example, Kytamer PC (pyrrolidone carboxylate) and Kytamer L (lactate) (these are manufactured by Union Carbide) may be exemplified.

10) Polyethylene Glycol

Specifically, polyethylene glycols having a number average molecular weight of from 1,200 to 40,000 are preferable. As commercially available products, for example, PEG-1540 and PEG-20000 (manufactured by Sanyo Chemical Industries, Ltd.) may be exemplified.

Of these set polymers, set polymers selected from acrylic-based polymers and vinylpyrrolidone-based polymers and polyethylene glycols are more preferable. The content of the set polymer is preferably from 0.01 to 20 mass %, more preferably from 0.05 to 10 mass %, even more preferably from 0.1 to 5 mass %, on the basis of the total mass of the hair cosmetic composition.

[Conditioning Component]

In order to further improve the conditioning effect, an oil agent, and a conditioning component selected from silicones other than the organopolysiloxanes of the components (A) and (B) may be incorporated into the hair cosmetic composition of the present invention.

The oil agent is used for improving the manageability of the hair after drying. Examples of the oil agent may include, for example, hydrocarbons such as squalene, squalane, liquid isoparaffins, light liquid isoparaffins, heavy liquid isoparaffins, α-olefin oligomers, liquid paraffins and cycloparaffins; glycerides such as castor oil, cacao oil, mink oil, avocado oil and olive oil; waxes such as beeswax, spermaceti, lanolin, microcrystalline wax, ceresine wax and carnauba wax; higher alcohols such as cetyl alcohol, oleyl alcohol, stearyl alcohol, isostearyl alcohol and 2-octyldodecanol; esters such as octyl dodecyl myristate, hexyl laurate, cetyl lactate, propylene glycol monostearate, oleyl oleate, hexadecyl 2-ethylhexanoate, isononyl isononanoate and tridecyl isononanoate; higher aliphatic acids such as capric acid, lauric acid, myristic acid, palmitic acid, stearic acid, behenic acid, oleic acid, palm oil aliphatic acids, isostearic acid and isopalmitic acid; and solid fats such as choresterol, vaseline, choresteryl isostearate and sphingolipids; as well as jojoba oil, isostearyl glyceryl ether, polyoxypropylene butyl ether. Among these, branched hydrocarbons such as squalene, squalane, liquid isoparaffins, light liquid isoparaffins, heavy liquid isoparaffins and α-olefin oligomers are more preferable.

The content of the oil agent is preferably from 0.01 to 20 mass %, more preferably from 0.05 to 10 mass %, even more preferably from 0.1 to 5 mass % in the hair cosmetic composition from the viewpoints of fine manageability and absence of stickiness.

Examples of the silicones may include, for example, dimethylpolysiloxane, polyether-modified silicones, amino-modified silicones, carboxy-modified silicones, methylphenylpolysiloxane, aliphatic acid-modified silicones, alcohol-modified silicones, aliphatic alcohol-modified silicones, epoxy-modified silicones, fluorine-modified silicones, cyclic silicones, alkyl-modified silicones. Among these, dimethylpolysiloxane, polyether-modified silicones and amino-modified silicones are preferable.

The dimethylpolysiloxane can impart fine lubricity to the hair, the polyether-modified silicones can impart smoothness to the hair, and the amino-modified silicones can impart moist feeling to the hair. In the present invention, one kind or two or more kinds of various silicones may be used depending on the performance demanded. As the dimethylpolysiloxane, from those having a viscosity of about 5 mm²/s to those having a viscosity of about 10,000,000 mm²/s, which are frequently provided as emulsions, can be used depending on the feeling demanded, and those having a viscosity of from 5,000 to 10,000,000 mm²/s are preferable, and those having a viscosity of from 50,000 to 10,000,000 mm²/s are more preferable.

The polyether-modified silicones may be silicones having a polyoxyalkylene group, and examples of the groups that constitute the polyoxyalkylene group may include, for example, an oxyethylene group and an oxypropylene group. More specific examples may include KF-6015, KF-945A, KF-6005, KF-6009, KF-6013, KF-6019, KF-6029, KF-6017, KF-6043, KF-353A, KF-354A and KF-355A (these are from Shin-Etsu Chemical Co., Ltd.), FZ-2404, SS-2805, FZ-2411, FZ-2412, SH3771M, SH3772M, SH3773M, SH3775M, SH3749, SS-280X series, BY22-008M, BY11-030 and BY25-337 (these are from Dow Corning Toray Co., Ltd.).

As the amino-modified silicones, those described in the CTFA Dictionary (USA, Cosmetic Ingredient Dictionary), the third edition under the name of Amodimethicone, which have an average molecular weight of from about 3,000 to 100,000, are preferable. Examples of commercially available products may include, for example, SM 8704C (Dow Corning Toray Co., Ltd.), DC 929 (Dow Corning Corporation), KT 1989 (GE Toshiba Silicones), 8500 Conditioning Agent, DOW CORNING TORAY SS-3588 and DOW CORNING TORAY SILSTYLE 104 (Dow Corning Toray Co., Ltd.).

The content of the silicones is preferably from 0.01 to 20 mass %, more preferably from 0.05 to 10 mass %, even more preferably from 0.5 to 5 mass % in the hair cosmetic composition of the present invention, from the viewpoints of finger combability and absence of stickiness.

[Organic Carboxylic Acid or Salt Thereof]

It is preferable that the hair cosmetic composition of the present invention further contains an organic carboxylic acid having 2 to 8 carbon atoms or a salt thereof. Examples of the organic carboxylic acid having 2 to 8 carbon atoms may include, for example, glycolic acid, lactic acid, citric acid, tartaric acid, malic acid, levulinic acid, acetatic acid, maleic acid, and fumaric acid. Among these, α-hydroxy acids are preferable, glycolic acid, citric acid, malic acid and lactic acid are preferable, and malic acid, lactic acid and citric acid are more preferable. Furthermore, examples of the salts thereof may include, for example, salts with alkali metals, alkaline earth metals, ammonia, and organic amine compounds. Two or more kinds of the organic acids or salts thereof may be used in combination.

Two or more kinds of these organic carboxylic acids or salts thereof may be used in combination, and it is preferable to use at least malic acid or a salt thereof. The content of the organic carboxylic acid or a salt thereof is preferably from 0.001 to 10 mass %, more preferably from 0.005 to 5 mass %, even more preferably from 0.01 to 3 mass % in terms of free acid, in the hair cosmetic composition of the present invention, from the viewpoints of an effect to reform the inner portion of the hair (for example, hollow repairement), an effect of improving firmness and elasticity after hair washing and an effect of imparting manageability to the hair.

[Organic Solvent]

It is preferable that the hair cosmetic composition of the present invention further contains an organic solvent selected from the group consisting of aromatic alcohols, N-alkylpyrrolidones, alkylene carbonates, polypropylene glycol, lactones and cyclic ketones.

As these organic solvents, those selected from the following i) to v) may be exemplified.

i) An aromatic alcohol represented by the general formula (6):

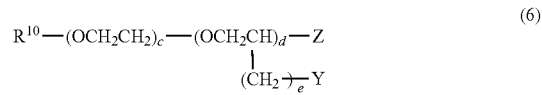

wherein $R^{10}$ represents a group $R^{11}$-Ph-$R^{12}$—($R^{11}$; a hydrogen atom, a methyl group or a methoxy group, $R^{12}$; a bond or a saturated or unsaturated divalent hydrocarbon group having 1 to 3 carbon atoms, Ph; a p-phenylene group), Y and Z each represent a hydrogen atom or a hydroxyl group, c, d and e each represent an integer of from 0 to 5, with the proviso that when c=d=0, Z is a hydroxyl group, and $R^{10}$ is not a group $R^{11}$-Ph-.

ii) An N-alkylpyrrolidone or N-alkylpyrrolidone in which an alkyl group or alkenyl group having 1 to 18 carbon atoms is bound to the nitrogen atom iii) An alkylene carbonate having 2 to 4 carbon atoms iv) A polypropylene glycol having a number average molecular weight of from 100 to 1,000 v) A lactone or cyclic ketone represented by the general formula (7), (8) or (9):

wherein X is a methylene group or an oxygen atom, $R^{13}$ and $R^{14}$ represent substituents that are different from each other, and f and g each represent 0 or 1.

Of these organic solvents, i) may include, for example, benzyl alcohol, cinnamyl alcohol, phenethyl alcohol, p-anisyl alcohol, p-methylbenzyl alcohol, phenoxyethanol, 2-benzyloxyethanol. ii) may include, for example, N-methylpyrrolidone, N-octylpyrrolidone, N-laurylpyrrolidone. iii) may include, for example, ethylene carbonate, propylene carbonate. As the polypropylene glycol having a number average molecular weight of 100 to 1,000 of iv), those having a number average molecular weight of 100 to 500 are preferable, and those having a polymerization degree of from 2 to 5 are further preferable. In v), as $R^{13}$ and $R^{14}$ in the general formulas (7) to (9), for example, linear, branched or cyclic alkyl groups, a hydroxyl group, a sulfate group, a phosphate group, a carboxy group, a phenyl group, a sulfoalkyl group, an alkyl phosphate group, a carboxyalkyl group are preferable, and specifically, linear or branched alkyl groups having 1 to 6 carbon atoms such as a methyl group, an ethyl group, a propyl group, an isopropyl group and a butyl group, in which the γ-position is substituted in the cases of γ-lactones, or the δ-position (i.e., the methylene adjacent to the heterooxygen atom) is substituted in the cases of δ-lactones, are preferable. Furthermore, in the cases when increase of the water-solubility of the compounds (7) to (9) is intended, it is preferable to have as $R^{13}$ or $R^{14}$, an acidic group such as a sulfate group, a phosphate group and a carboxy group, or an alkyl group substituted with these groups. Among v), the lactones may include, for example, γ-butyrolactone, γ-caprolactone, γ-valerolactone, δ-valerolactone, δ-caprolactone, and δ-heptanolactone. From the viewpoint of the stability of the lactones, γ-lactones are preferable, and among these, γ-butyrolactone and γ-caprolactone are more preferable. Among v), the cyclic ketones may include, for example, cyclopentanone, cyclohexanone, cycloheptanone, and 4-methylcycloheptanone.

More preferable organic solvents may include benzyl alcohol, benzyloxyethanol, propylene carbonate and polypropylene glycol (number average molecular weight: 300 to 500, specifically 400).

Furthermore, the organic solvent used in the present invention is preferably liquid form at 25° C. and required to have a ClogP of from −2 to 3, and the ClogP is preferably from −1 to 2 in terms of promotion of penetration. The ClogP as used here is a scale that represents distribution of a substance between an octanol phase and an aqueous phase, which is a calculated value of an octanol-water-distribution coefficient (logP) defined by the formula below, and the examples are described in Chemical Reviews, Vol. 71, 6 (1971).

$$\log P = \log([Substance]_{Octanol}/[Substance]_{Water})$$

wherein $[Substance]_{Octanol}$ represents a molar concentration of the substance in a 1-octanol phase, and $[Substance]_{Water}$ represents a molar concentration of the substance in an aqueous phase.

The ClogPs of major organic solvents are specifically shown as follows: benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41) and γ-butyrolactone (−0.64).

Two or more kinds of these organic solvents may be used in combination, and the content thereof is preferably from 0.001 to 20 mass %, more preferably from 0.01 to 10 mass %, even more preferably from 0.05 to 5 mass %, from the viewpoints of feeling of use, gloss of the hair and promotion of refining effects (for example, improvement of elasticity, improvement of humidity resistance).

The mass ratio of the above-mentioned organic carboxylic acid or a salt thereof and the organic solvent is preferably (organic carboxylic acid or a salt thereof):(organic solvent)=10:1 to 1:7, more preferably in the range of from 4:1 to 1:3, so as to effectively express, for example, an effect to reform the inner portion of the hair (for example, hollow repairement), an effect of improving lasting of a set, an effect of improving manageability.

Besides the above-mentioned components, components that are used in general hair cosmetics composition may be suitably incorporated into the hair cosmetic composition of the present invention depending on the purpose. Examples of such components may include, for example, antidandruff agents; vitamins; bactericides; anti-inflammatory drugs; chelating agent; humectants such as sorbitol and panthenol; coloring agents such as dyes and pigments; viscosity adjusting agents such as hydroxyethyl cellulose, methyl cellulose, polyethylene glycol and clay minerals; pH adjusting agents such as sodium hydroxide and potassium hydroxide; plant extracts; pearlescent agents; fragrances; pigments; ultra-violet ray absorbers; anti-oxidants; and other components described in the "ENCYCLOPEDIA OF SHAMPOO INGREDIENTS (MICELLE PRESS)".

[pH]

The hair cosmetic composition of the present invention has a pH at 25° C. when diluted with water by 20-fold by mass of preferably from 2.5 to 7.0, more preferably a pH of from 2.5 to 6.0, even more preferably a pH of from 3.0 to 5.0.

The form of the hair cosmetic composition of the present invention may be suitably selected from, for example, a liquid, a gel-form, a foam, a paste-form, and an emulsion, and a liquid using water and/or the above-mentioned aliphatic alcohol having 1 to 6 carbon atoms as a solvent is preferable.

The hair cosmetic composition of the present invention is preferably a leave-on type hair cosmetic composition that is used without rinsing the hair cosmetic composition away after application onto the hair, and is preferably used as, for example, a hair styling agent, and a hair conditioning agent. Examples of formulations may include, for example, a pump spray, an aerosol spray, a pump form, an aerosol form, a gel, a lotion, and a cream.

[Hair Treatment Method]

The hair cosmetic composition of the present invention can provide a desired hair styling effect by finishing by blow-drying or natural drying without rinsing the hair cosmetic composition away after application onto the hair. In the drying of the hair after application of the hair cosmetic composition, the hair may be left as it is, a hair refining effect can be obtained by blow drying. As used herein, "without rinsing away" means that the interval from the time at which the hair cosmetic composition is applied to the hair to the time of the next hair washing is at least 3 hours or more, preferably to 6 hours or more.

Furthermore, the effect of the present invention can further be enhanced by warming after the application of the hair cosmetic composition to the hair. For the warming, for example, a dryer, a heater, a trowel, or an iron may be used. In the case when, for example, a dryer or a heater is used, the temperature is preferably from 60° C. to 150° C., more preferably from 70° C. to 120° C. The time for warming is preferably from 10 seconds to 30 minutes, more preferably from 20 seconds to 20 minutes, even more preferably from 30 seconds to 10 minutes. In the case when, for example, a trowel or an iron is used, the temperature is preferably from 80° C. to 250° C., even more preferably from 100° C. to 200° C. The time for warming is preferably from 0.5 second to 3 minutes, more preferably from 1 second to 2 minutes, even more preferably from 2 seconds to 30 seconds. Furthermore, the interval time from the application of the hair cosmetic composition to the heating/warming is preferably within 1 hour, more preferably within 45 minutes, even more preferably within 30 minutes.

The preferable embodiments of the present invention are shown below.

[1] A hair cosmetic composition comprising the following components (A) and (B) at a mass ratio of (A)/(B)=0.66 to 9.0:

component (A): an organopolysiloxane, wherein poly(N-acylalkyleneimine) segments consisting of repeating units represented by the following general formula (1);

wherein R¹ represents a hydrogen atom, an alkyl group having 1 to 22 carbon atoms, an aralkyl group or an aryl group, and n represents 2 or 3, are bound to at least two silicon atoms of an organopolysiloxane segment that constitutes a main chain via alkylene groups containing heteroatoms, wherein the number average molecular weight of the poly (N-acylalkyleneimine) segments is from 1,200 to 5,500, the mass ratio of (a) the organopolysiloxane segment that constitutes the main chain and (b) the poly(N-acylalkyleneimine) segments (a/b) is from 35/65 to 60/40, the weight average molecular weight of the organopolysiloxane segment between the adjacent poly(N-acylalkyleneimine) segments is from 1,300 to 5,500, and the weight average molecular weight of the organopolysiloxane segment that constitutes the main chain is from 7,000 to 100,000; and component (B): an organopolysiloxane, wherein poly(N-acylalkyleneimine) segments consisting of repeating units represented by the above-mentioned general formula (1) are bound to at least two silicon atoms of the organopolysiloxane segment that constitutes a main chain via alkylene groups containing heteroatoms, wherein the number average molecular weight of the poly (N-acylalkyleneimine) segments is from 800 to 1,600, the mass ratio of (a) the organopolysiloxane segment that constitutes the main chain and (b) the poly(N-acylalkyleneimine) segments (a/b) is from 65/35 to 82/18, the weight average molecular weight of the organopolysiloxane segment between the adjacent poly(N-acylalkyleneimine) segments is from 1,500 to 3,500, and the weight average molecular weight of the organopolysiloxane segment that constitutes the main chain is from 10,000 to 100,000.

[2] The hair cosmetic composition according to [1], wherein the mass ratio of the components (A) and (B), (A)/(B)=0.90 to 7.0.

[3] The hair cosmetic composition according to [1], wherein the mass ratio of the components (A) and (B), (A)/(B)=1.0 to 5.6.

[4] The hair cosmetic composition according to [1], wherein the mass ratio of the components (A) and (B), (A)/(B)=1.0 to 4.0.

[5] The hair cosmetic composition according to any of [1] to [4], wherein the mass ratio of (a) the organopolysiloxane segment that constitutes the main chain and (b) the poly(N-acylalkyleneimine) segments (a/b) in component (A) is from 42/58 to 58/42.

[6] The hair cosmetic composition according to any of [1] to [4], wherein the mass ratio of (a) the organopolysiloxane segment that constitutes the main chain and (b) the poly(N-acylalkyleneimine) segments (a/b) in component (A) is from 45/55 to 55/45.

[7] The hair cosmetic composition according to any of [1] to [4], wherein the mass ratio of (a) the organopolysiloxane segment that constitutes the main chain and (b) the poly(N-acylalkyleneimine) segments (a/b) in component (A) is from 47/53 to 53/47.

[8] The hair cosmetic composition according to any of [1] to [7], wherein the mass ratio of (a) the organopolysiloxane segment that constitutes the main chain and (b) the poly(N-acylalkyleneimine) segments (a/b) in component (B) is from 68/32 to 80/20.

[9] The hair cosmetic composition according to any of [1] to [7], wherein the mass ratio of (a) the organopolysiloxane segment that constitutes the main chain and (b) the poly(N-acylalkyleneimine) segments (a/b) in component (B) is from 70/30 to 79/21.

[10] The hair cosmetic composition according to any of [1] to [7], wherein the mass ratio of (a) the organopolysiloxane segment that constitutes the main chain and (b) the poly(N-acylalkyleneimine) segments (a/b) in component (B) is from 73/27 to 79/21.

[11] The hair cosmetic composition according to any of [1] to [10], wherein R¹ is an alkyl group having 1 to 6 carbon atoms in the general formula (1).

[12] The hair cosmetic composition according to any of [1] to [11], wherein the content of component (A) is from 0.01 to 30 mass %, and the content of component (B) is from 0.001 to 30 mass %.

[13] The hair cosmetic composition according to [12], wherein the content of component (A) is from 0.05 to 20 mass %.

[14] The hair cosmetic composition according to [12], wherein the content of component (A) is from 0.1 to 10 mass %.

[15] The hair cosmetic composition according to [12], wherein the content of component (A) is from 0.5 to 5 mass %.

[16] The hair cosmetic composition according to any of [11] to [15], wherein the content of component (B) is from 0.005 to 20 mass %.

[17] The hair cosmetic composition according to any of [11] to [15], wherein the content of component (B) is from 0.01 to 10 mass %.

[18] The hair cosmetic composition according to any of [11] to [15], wherein the content of component (B) is from 0.05 to 5 mass %.

[19] The hair cosmetic composition according to any of [1] to [18], further comprising water and/or an aliphatic alcohol having 1 to 6 carbon atoms.

[20] The hair cosmetic composition according to [19], wherein the content of the aliphatic alcohol having 1 to 6 carbon atoms is from 0.01 to 98 mass %.

[21] The hair cosmetic composition according to any of [1] to [20], further comprising a cationic surfactant.

[22] The hair cosmetic composition according to [21], wherein the cationic surfactant comprises a quaternary ammonium salt represented by the following general formula (5):

(5)

wherein R⁸ and R⁹ each independently represent a hydrogen atom, an alkyl group having 1 to 28 carbon atoms or a benzyl group, with the proviso that the case when R⁸ and R⁹ are simultaneously hydrogen atoms or benzyl groups, and the case when R⁸ and R⁹ are simultaneously lower alkyl groups having 1 to 3 carbon atoms are excluded, and Z⁻ represents an anion.

[23] The hair cosmetic composition according to [21] or [22], wherein the content of the cationic surfactant is from 0.01 to 10 mass %.

[24] The hair cosmetic composition according to any of [1] to [23], which is used without rinsing the hair cosmetic composition away after application onto hair.

[25] A method for treating hair, comprising applying the hair cosmetic composition according to [24] onto the hair, and next blow-drying or natural drying without rinsing the hair cosmetic composition away.

EXAMPLES

Synthesis Example 1

Organopolysiloxane A 6.17 g (0.04 mol) of diethyl sulfate and 93.8 g (0.947 mol) of 2-ethyl-2-oxazoline were dissolved in 203 g of dehydrated ethyl acetate and refluxed under a nitrogen atmosphere for 8 hours under heating to thereby synthesize an end-reactive poly(N-propionylethyleneimine). The number average molecular weight was measured by GPC and found to be 2,500. A 33% ethyl acetate solution of 100 g of a side chain primary aminopropyl-modified polydimethylsiloxane (weight average molecular weight: 30,000, amine equivalent amount: 2,000) was added thereto in a lump, and reflux was conducted under heating for 10 hours. The reaction mixture was concentrated under a reduced pressure to give an N-propionylethyleneimine-dimethylsiloxane copolymer as a pale yellow solid (190 g, yield 95%). The content rate of the organopolysiloxane segment in the final product was 50 mass %, and the weight average molecular weight was 60,000. As a result of neutralization titration with hydrochloric acid using methanol as a solvent, it was found that about 20 mol % of amino groups remained.

Synthesis Example 2

Organopolysiloxane B 5.92 g (0.038 mol) of diethyl sulfate and 60.7 g (0.613 mol) of 2-ethyl-2-oxazoline were dissolved in 135 g of dehydrated ethyl acetate and refluxed under a nitrogen atmosphere for 8 hours under heating to thereby synthesize an end-reactive poly(N-propionylethyleneimine). The number average molecular weight was measured by GPC and found to be 1,700. A 33% ethyl acetate solution of 100 g of a side chain primary aminopropyl-modified polydimethylsiloxane (weight average molecular weight: 30,000, amine equivalent amount: 1,980) was added thereto in a lump, and reflux was conducted under heating for 10 hours. The reaction mixture was concentrated under a reduced pressure to give an N-propionylethyleneimine-dimethylsiloxane copolymer as a pale yellow solid (158 g, yield 95%). The content rate of the organopolysiloxane segment in the final product was 60 mass %, and the weight average molecular weight was 50,000. As a result of neutralization titration with hydrochloric acid using methanol as a solvent, it was found that about 24 mol % of amino groups remained.

Synthesis Example 3

Organopolysiloxane C 19.0 g (0.12 mol) of diethyl sulfate and 81.0 g (0.82 mol) of 2-ethyl-2-oxazoline were dissolved in 203.0 g of dehydrated ethyl acetate and refluxed under a nitrogen atmosphere for 8 hours under heating to thereby synthesize an end-reactive poly(N-propionylethyleneimine) in a similar manner to that of Synthesis Example 1. The number average molecular weight was measured by GPC and found to be 1,100. A 33% ethyl acetate solution of 300 g of a side chain primary aminopropyl-modified polydimethylsiloxane (weight average molecular weight: 32,000, amine equivalent amount: 2,000) was added thereto in a lump, and reflux was conducted under heating for 10 hours. The reaction mixture was concentrated under a reduced pressure to give an N-propionylethyleneimine-dimethylsiloxane copolymer as a pale yellow rubbery solid (390 g, yield 97%). The content rate of the silicone segment in the final product was 75 mass %, and the weight average molecular weight was 40,000. As a result of neutralization titration with hydrochloric acid using methanol as a solvent, it was found that about 20 mol % of amino groups remained.

Synthesis Example 4

Organopolysiloxane D 0.77 g (0.005 mol) of diethyl sulfate and 12.9 g (0.13 mol) of 2-ethyl-2-oxazoline were dissolved in 28 g of dehydrated ethyl acetate and refluxed under a nitrogen atmosphere for 8 hours under heating to thereby synthesize an end-reactive poly(N-propionylethyleneimine). The number average molecular weight was measured by GPC and found to be 2,700. A 33% ethyl acetate solution of 100 g of a side chain primary aminopropyl-modified polydimethylsiloxane (weight average molecular weight: 100,000, amine equivalent amount: 20,000) was added thereto in a lump, and reflux was conducted under heating for 10 hours. The reaction mixture was concentrated under a reduced pressure to give an N-propionylethyleneimine-dimethylsiloxane copolymer as a colorless solid (108 g, yield 95%). The content rate of the organopolysiloxane segment in the final product was 88 mass %, and the weight average molecular weight was 114,000. As a result of neutralization titration with hydrochloric acid using methanol as a solvent, it was found that no amino groups remained.

Examples 1 to 7 and Comparative Examples 1 to 6

The hair cosmetic compositions shown in Table 1 were each prepared according to a conventional method, and Evaluation 1 (volume hair style test) and Evaluation 2 (frizzy hair test) were conducted according to the following methods.

[Evaluation 1] Volume Hair Style Test

"Degree of volume", "smoothness of finger combing through volume hair style" and "retention of volume" were evaluated.

"Degree of Volume"

A wig manufactured by Beaulax Co., Ltd. (No. 775S, average hair diameter: about 50 μm) is cut so that the hair length becomes a medium length. The wig was washed with a plain shampoo (Curél shampoo manufactured by Kao Corporation, this shall also apply hereinafter) and towel-dried, and 4 g of the hair treatment agent described in Examples or Comparative Examples was applied onto the entirety of the hair of the wig by a pump dispenser (the spray particle size upon ejection was from 50 to 100 μm) and was applied thoroughly onto the entirety with a large-tooth comb. Thereafter the wig was dried by hot air from a blow dryer (Ionity EH5305P manufactured by Panasonic Corporation). The procedures of the drying comprised first conducting drying while running one hand through the hair so that hot air reaches the root of the wig hair, and subsequently drying the entirety of the hair.

With respect to the degree of volume of the finished hair style, using the finish in the case of finishing in a similar manner by applying only 4 g of purified water instead of the hair treatment agent as a criterion, the following 4-stage sensory evaluation was conducted by five expert panelists.

4 points: the volume is apparently larger than that of the criterion, 3 points: the volume is somewhat larger than that of the criterion, 2 points: the volume is slightly larger than that of the criterion, 1 point: the volume is similar to or smaller than that of the criterion.

The evaluation result was obtained by summing up the points of the 5 panelists, according to the following criteria.
A: 17 to 20 points
B: 13 to 16 points
C: 9 to 12 points
D: 5 to 8 points "Smoothness of Finger Combing Through Volume Hair Style"

With respect to the smoothness of finger combing through a volume hair style in the wig that was finished by the above-mentioned hair styling procedure, using the finger combing in the case of finishing in a similar manner by applying only 4 g of purified water instead of the hair treatment agent as a criterion, the following 4-stage sensory evaluation was conducted by five expert panelists.

4 points: the smoothness is apparently higher than that of the criterion, 3 points: the smoothness is somewhat higher than that of the criterion, 2 points: the smoothness is slightly higher than that of the criterion, 1 point: the smoothness is similar to or less than that of the criterion.

The evaluation result was obtained by summing up the points of the 5 panelists, according to the following criteria.
A: 17 to 20 points
B: 13 to 16 points
C: 9 to 12 points
D: 5 to 8 points "Retention of Volume"

With respect to the retention of a volume hair style after leaving the wig that was finished by the above-mentioned hair styling procedure under an environment at 25° C. and a relative humidity of 50% for 3 hours, using the retention property of the hair style in the case of finishing in a similar manner by applying only 4 g of purified water instead of the hair treatment agent as a criterion, the following 4-stage sensory evaluation was conducted by five expert panelists.

4 points: the volume is apparently larger than that of the criterion, 3 points: the volume is somewhat larger than that of the criterion, 2 points: the volume is slightly larger than that of the criterion, 1 point: the volume is similar to or smaller than that of the criterion.

The evaluation result was obtained by summing up the points of the 5 panelists, according to the following criteria.
A: 17 to 20 points
B: 13 to 16 points
C: 9 to 12 points
D: 5 to 8 points

[Evaluation 2] Hair Styling Effect on Frizzy Hair

"Manageability of cowlick of frizzy hair", "softness of finish of frizzy hair" and "retention of manageability of frizz tips" were evaluated.

"Manageability of Flyaways of Frizzy Hair"

Hair bundles each having a length of 30 cm and a weight of 10 g were prepared by using chemically untreated curly frizzy hair derived from European and American women, and used in the evaluation. Each hair bundle was washed using a plain shampoo and towel-dried, and 0.5 g of the hair treatment agent described in Examples or Comparative Examples was applied onto the entirety of the surface and rear surface of the hair bundle by a pump dispenser (the spray particle size upon ejection was from 50 to 100 μm) and was applied thoroughly onto the entirety with a large-tooth comb. Thereafter the curl bundle was scrunched 5 times by using one hand in such a manner that the curl bundle was cupped in the hand, and natural-dried by leaving under an environment at 25° C. and a relative humidity of 50% for 1 hour and 30 minutes. With respect to the manageability of the finished hair style, using the finish in the case of finishing in a similar manner by applying only 0.5 g of purified water instead of the hair treatment agent as a criterion, the following 4-stage sensory evaluation was conducted by five expert panelists.

4 points: the manageability is apparently higher than that of the criterion, 3 points: the manageability is somewhat higher than that of the criterion, 2 points: the manageability is slightly higher than that of the criterion, 1 point: the manageability is similar to or less than that of the criterion.

The evaluation result was obtained by summing up the points of the 5 panelists, according to the following criteria.

A: 17 to 20 points

B: 13 to 16 points

C: 9 to 12 points

D: 5 to 8 points

"Softness of Finish of Frizzy Hair"

With respect to the softness of the finish in the hair bundle that was finished by the above-mentioned hair styling procedure, using the softness in the case of finishing in a similar manner by applying only 0.5 g of purified water instead of the hair treatment agent as a criterion, the following 4-stage sensory evaluation was conducted by five expert panelists.

4 points: the softness is apparently higher than that of the criterion, 3 points: the softness is somewhat higher than that of the criterion, 2 points: the softness is slightly higher than that of the criterion, 1 point: the softness is similar to or less than that of the criterion.

The evaluation result was obtained by summing up the points of the 5 panelists, according to the following criteria.

A: 17 to 20 points

B: 13 to 16 points

C: 9 to 12 points

D: 5 to 8 points

"Retention of Manageability of Frizz Hair"

With respect to the retention of manageability after standing still the hair bundle that was finished by the above-mentioned hair styling procedure, under an environment at 25° C. and a relative humidity of 90% for 1 hour, using the retention of manageability in the case of finishing in a similar manner by applying only 0.5 g of purified water instead of the hair treatment agent as a criterion, the following 4-stage sensory evaluation was conducted by five expert panelists.

4 points: the manageability is apparently higher than that of the criterion, 3 points: the manageability is somewhat higher than that of the criterion, 2 points: the manageability is slightly higher than that of the criterion, 1 point: the manageability is similar to or less than that of the criterion.

The evaluation result was obtained by summing up the points of the 5 panelists, according to the following criteria.

17 to 20 points

B: 13 to 16 points

C: 9 to 12 points

D: 5 to 8 points

TABLE 1

| | Mass % | Examples | | | | | | | Comparative Examples | | | | | |
|---|---|---|---|---|---|---|---|---|---|---|---|---|---|---|
| | | 1 | 2 | 3 | 4 | 5 | 6 | 7 | 1 | 2 | 3 | 4 | 5 | 6 |
| (A) | Organopolysiloxane A | 2.5 | 2 | 2.5 | — | 1.45 | 2.75 | 2.95 | 3.3 | — | — | 2.5 | 1.2 | 2.5 |
| | Organopolysiloxane B | — | — | — | 2.7 | — | — | — | — | — | 3.3 | — | — | — |
| (B) | Organopolysiloxane C | 0.75 | 1.3 | 0.75 | 0.6 | 1.85 | 0.55 | 0.35 | — | 3.3 | — | 0.2 | 2 | — |
| (B') | Organopolysiloxane D | — | — | 0.75 | — | — | — | — | — | — | — | — | — | 0.75 |
| | Ethanol (99.5%) | 10.0 | 10.0 | 10.0 | 10.0 | 10.0 | 10.0 | 10.0 | 10.0 | 10.0 | 10.0 | 10.0 | 10.0 | 10.0 |
| | Stearyltrimethylammonium chloride | 0.2 | 0.2 | 0.2 | 0.2 | 0.2 | 0.2 | 0.2 | 0.2 | 0.2 | 0.2 | 0.2 | 0.2 | 0.2 |
| | Purified water | Balance | Balance | Balance | Balance | Balance | Balance | Balance | Balance | Balance | Balance | Balance | Balance | Balance |
| | Silicone rate (*) | 55.8 | 59.8 | 61.8 | 62.7 | 64.0 | 54.2 | 52.7 | 50.0 | 75.0 | 60.0 | 51.9 | 65.6 | 58.8 |
| | Mass ratio (A)/(B) | 3.3 | 1.5 | 3.3 | 4.5 | 0.8 | 5 | 8.4 | — | — | — | 12.5 | 0.6 | — |
| Evaluation 1 | Degree of volume | A (20) | B (15) | A (20) | B (14) | B (16) | A (20) | A (20) | B (15) | C (10) | C (9) | B (15) | C (12) | B (16) |
| | Smoothness of finger combing after finishing | A (19) | A (18) | A (20) | B (15) | A (18) | A (18) | A (18) | B (15) | B (15) | B (16) | A (17) | A (18) | A (19) |
| | Retention of volume | A (19) | B (14) | A (20) | B (13) | C (12) | A (17) | B (15) | C (12) | D (8) | D (7) | C (11) | C (10) | C (9) |
| Evaluation 2 | Manageability of flyaways of frizzy hair | A (18) | A (20) | A (19) | B (13) | B (16) | A (18) | B (15) | B (13) | B (16) | C (11) | B (14) | B (16) | C (11) |
| | Softness of finish of frizzy hair | A (17) | A (18) | A (20) | B (15) | A (17) | A (18) | B (16) | C (12) | A (19) | B (16) | B (15) | A (17) | A (18) |
| | Retention of manageability of frizzy hair | B (16) | A (19) | B (16) | B (13) | B (16) | B (15) | C (11) | C (12) | B (15) | D (8) | C (10) | C (12) | D (8) |

*Parts by mass that is accounted for by the organopolysiloxane segment in 100 parts by mass of the whole organopolysiloxane (mass average)

The invention claimed is:

1. A hair cosmetic composition comprising components (A) and (B) at a mass ratio of (A)/(B)=0.66 to 9.0:

component (A): an organopolysiloxane, wherein poly(N-acylalkyleneimine) segments consisting of repeating units represented by general formula (I):

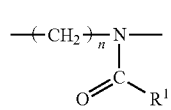

(1)

wherein $R^1$ represents a hydrogen atom, an alkyl group having 1 to 22 carbon atoms, an aralkyl group or an aryl group, and n represents 2 or 3, are bound to at least two silicon atoms of an organopolysiloxane segment that constitutes a main chain via alkylene groups containing heteroatoms, wherein the number average molecular weight of the poly(N-acylalkyleneimine) segment is from 1,200 to 5,500, the mass ratio of (a) the organopolysiloxane segment that constitutes the main chain and (b) the poly(N-acylalkyleneimine) segments (a/b) is from 35/65 to 60/40, the weight average molecular weight of the organopolysiloxane segment between adjacent poly(N-acylalkyleneimine) segments is from 1,300 to 5,500, and the weight average molecular weight of the organopolysiloxane segment that constitutes the main chain is from 7,000 to 100,000; and component (B): an organopolysiloxane, wherein poly(N-acylalkyleneimine) segments consisting of repeating units represented by the general formula (I) are bound to at least two silicon atoms of an organopolysiloxane segment that constitutes a main chain via alkylene groups containing heteroatoms, wherein the number average molecular weight of the poly(N-acylalkyleneimine) segments is from 800 to 1,600, the mass ratio of (a) the organopolysiloxane segment that constitutes the main chain and (b) the poly(N-acylalkyleneimine) segments (a/b) is from 65/35 to 82/18, the weight average molecular weight of the organopolysiloxane segment between the adjacent poly(N-acylalkyleneimine) segments is from 1,500 to 3,500, and the weight average molecular weight of the organopolysiloxane segment that constitutes the main chain is from 10,000 to 100,000.

2. The hair cosmetic composition according to claim 1, wherein the mass ratio of the components (A) and (B), (A)/(B)=1.0 to 5.6.

3. The hair cosmetic composition according to claim 1, wherein the mass ratio of (a) the organopolysiloxane segment that constitutes the main chain and (b) the poly(N-acylalkyleneimine) segments (a/b) in component (A) is from 42/58 to 58/42.

4. The hair cosmetic composition according to claim 1, wherein the mass ratio of (a) the organopolysiloxane segment that constitutes the main chain and (b) the poly(N-acylalkyleneimine) segments (a/b) in component (B) is from 68/32 to 80/20.

5. The hair cosmetic composition according to claim 1, wherein $R^1$ is an alkyl group having 1 to 6 carbon atoms in general formula (1).

6. The hair cosmetic composition according to claim 1, wherein the content of component (A) is from 0.01 to 30 mass %, and the content of component (B) is from 0.001 to 30 mass %.

7. The hair cosmetic composition according to claim 1, further comprising water, an aliphatic alcohol having 1 to 6 carbon atoms, or a combination thereof.

8. The hair cosmetic composition according to claim 1, further comprising a cationic surfactant.

9. The hair cosmetic composition according to claim 8, wherein the cationic surfactant comprises a quaternary ammonium salt represented by general formula (5):

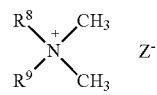
(5)

wherein $R^8$ and $R^9$ each independently represents a hydrogen atom, an alkyl group having 1 to 28 carbons or a benzyl group, with the proviso that the case when $R^8$ and $R^9$ are simultaneously hydrogen atoms or benzyl groups, and the case when $R^8$ and $R^9$ are simultaneously lower alkyl groups having 1 to 3 carbon atoms are excluded, and $Z^-$ represents an anion.

10. The hair cosmetic composition according to claim 8, wherein the content of the cationic surfactant is from 0.01 to 10 mass %.

11. The hair cosmetic composition according to claim 1, which is used without being rinsed away after application onto hair.

12. A method for treating hair, comprising applying the hair cosmetic composition according to claim 11 onto the hair, and next blow-drying or natural drying without rinsing the hair cosmetic composition away.

* * * * *